(12) United States Patent
Kuo et al.

(10) Patent No.: US 6,436,721 B1
(45) Date of Patent: Aug. 20, 2002

(54) DEVICE AND METHOD FOR OBTAINING CLINICALLY SIGNIFICANT ANALYTE RATIOS

(75) Inventors: Hai-Hang Kuo, Granger; Carol A. Miller, Elkhart; Dayaweera Wijesuriya, Granger; Meitak Teresa Yip; Chris T. Zimmerle, both of Elkhart, all of IN (US)

(73) Assignee: Bayer Corporation, Elkhart, IN (US)

( * ) Notice: Subject to any disclaimer, the term of this patent is extended or adjusted under 35 U.S.C. 154(b) by 584 days.

(21) Appl. No.: 08/900,586

(22) Filed: Jul. 25, 1997

(51) Int. Cl.[7] ............... G01N 33/558; G01N 33/53; G01N 33/00; G01N 33/546
(52) U.S. Cl. ............ 436/514; 435/7.1; 435/973; 436/98; 436/518; 436/534; 436/909
(58) Field of Search .............. 435/7.1, 973; 436/98, 436/514, 518, 534, 909

(56) References Cited

U.S. PATENT DOCUMENTS

| | | | |
|---|---|---|---|
| 3,615,229 A | * 10/1971 | Besch et al. | 23/230 |
| 4,446,232 A | 5/1984 | Liotta | 435/7 |
| 4,703,017 A | 10/1987 | Campbell et al. | 436/501 |
| 4,868,108 A | 9/1989 | Bahar et al. | 435/7 |
| 4,943,522 A | 7/1990 | Eisinger et al. | 435/7 |
| 5,385,847 A | * 1/1995 | Yip et al. | 436/534 |
| 5,500,350 A | * 3/1996 | Baker et al. | 435/7.92 |
| 5,569,608 A | 10/1996 | Sommer | 436/518 |

FOREIGN PATENT DOCUMENTS

| | | | |
|---|---|---|---|
| EP | 0462376 | 12/1991 | G01N/33/543 |
| WO | WO 96/34271 | 10/1996 | G01N/21/00 |
| WO | WO 96/04554 | 12/1996 | G01N/33/52 |

* cited by examiner

Primary Examiner—Rodney P Swartz
(74) Attorney, Agent, or Firm—Jerome L. Jeffers

(57) ABSTRACT

Disclosed is a method for determining the concentration of an analyte in a sample of body fluid. The method involves contacting the body fluid sample with a test strip containing mobile, labeled specific binding partner for the analyte, through which strip the test fluid, analyte and any complex formed by interaction of the analyte and labeled specific binding partner therefore can flow by capillarity. The strip contains at least one zone for capture of the labeled specific binding partner and at least one separate zone for retention of the analyte/labeled specific binding partner complex. By determining the magnitude of the signal from the detectable label in the capture zone(s) and retention zone(s) and determining a final response signal by correlating signals using an algorithm and number of zones chosen in a manner that provides a final response signal best suited for the particular assay, the concentration of the analyte can be determined with greater precision.

13 Claims, 2 Drawing Sheets

DEVICE AND METHOD FOR OBTAINING CLINICALLY SIGNIFICANT ANALYTE RATIOS

BACKGROUND OF THE INVENTION

Immunochromatographic strip formats have become increasingly popular for qualitative and semi-quantitative assays which use visual detection schemes. This type of immunoassay involves the application of a liquid test sample suspected of containing an analyte to be detected to an application zone of an immunochromatographic test strip. The strip is comprised of a matrix material through which the test fluid and analyte suspended or dissolved therein can flow by capillarity from the application zone to a capture zone where a detectable signal, or the absence of such, reveals the presence of the analyte. Typically, the strip will include means for immunospecifically binding the analyte to be detected with its specific binding partner which bears the detectable label. In one such scheme, as disclosed in U.S. Pat. No. 4,446,232; the strip contains an enzyme labeled, mobile binding partner for the analyte which is in a zone downstream from the sample application zone. If analyte is present in the test sample, it will combine with its labeled binding partner to form a complex which will flow along the strip to a detection zone which contains a substrate for the enzyme label which is capable of providing a colored response in the presence of the enzyme label. The strip may contain a zone in which analyte is immobilized, so that labeled binding partner which does not combine with analyte, due to the absence of analyte in the sample, will be captured and thereby inhibited from reaching the detection zone. There have been published various modifications of this technique, all of which involve some competitive specific binding system in which the presence or absence of analyte in the test sample is determined by the detection or lack thereof of labeled binding partner in the capture zone.

An alternative to the above described immunometric assay which detects the free labeled antibody is the so called sandwich format in which the capture zone contains immobilized antibodies against an epitope of the analyte which is different than the epitope to which the labeled antibody is specific. In this format, there is formed a sandwich of the analyte between the immobilized and labeled antibodies and it is therefore an immunometric assay which detects the bound labeled antibody species.

Not all of the schemes for immunochromatography rely on an enzyme labeled binding partner/enzyme substrate for providing the signal for detection of the analyte. In U.S. Pat. No. 4,806,311 there is disclosed a multizone test device for the specific binding assay determination of an analyte and an immobilized binding partner therefore together with a capture zone for receiving labeled reagent which migrates thereto from the reagent zone. The capture zone contains an immobilized form of a binding substance for the labeled reagent. The labeled reagent bears a chemical group having a detectable physical property which is detectable on the basis of its own physical properties, so that it does not require a chemical reaction with another substance. Exemplary of such groups are colored species of fluorescers, phosphorescent molecules, radioisotopes and electroactive moieties.

U.S. Pat. No. 4,703,017 describes the use of visible particulate labels for the receptor. Various particulate labels such as gold sol particles and visible dye containing liposomes are mentioned.

In WO-96/34271 there is disclosed a device for determining a target analyte and creatinine in a fluid test sample which device has an assay strip for the detection of creatinine and a second assay strip for the detection of the target analyte. The creatinine concentration may be determined calorimetrically or by the specific capture of labeled creatinine binding partners. The concentration of the target analyte is corrected based on the sample's creatinine concentration which correction can either be done manually or by means of a properly programmed reflectance analyzer.

EP 0 462 376 $A_2$ discloses an immunochromatographic procedure in which signal at the capture site and the conjugate recovery site of the strip are detected and the analyte concentration is determined by the intensity of the signal at the capture site relative to the signal at the conjugate recovery site. Also of interest in this regard is U.S. Pat. No. 5,569,608.

Immunochromatographic strip formats provide a viable system for the determination of various analytes (whether they be antigens or antibodies) but suffer from the limitation that they yield results which are at best semi-quantitative when, for some analytes, more precise, quantitative results are required. Accordingly, it would be desirable and it is an object of the present invention to provide a means for quantifying the results of analyses carried out by the use of immunochromatographic strip formats.

SUMMARY OF THE INVENTION

The present invention involves a method for determination of an analyte in a sample of body fluid which comprises the steps of:

a) providing a test strip comprising a matrix through which the fluid sample can flow by capillarity, said strip having a first region which contains mobile specific binding partner for the analyte which binding partner bears a detectable label and can react with the analyte to form an analyte/labeled binding partner complex, at least one second region which contains immobilized analyte or an immobilized binding partner which is specific for an epitope of the analyte different than that to which the labeled binding partner is specific, at least one third region which contains means for capturing the analyte/labeled specific binding partner complex which is not bound in the second region and a fourth region which contains means for producing a detectable signal the intensity of which corresponds to the level of a second analyte whose concentration is clinically related to that of the analyte whose concentration in the body fluid is being determined;

b) developing the matrix by applying a sample of a body fluid suspected of containing the first and second analytes thereto thereby allowing it to contact the labeled specific binding partner so that the analyte present in the fluid sample binds to the labeled specific binding partner to form a complex while leaving excess, unreacted labeled binding partner free to further react whereby the fluid sample carries the analyte/labeled partner complex and unreacted labeled binding partner along the matrix by capillarity to the second region containing the immobilized analyte in which region unreacted labeled binding partner is bound to the immobilized analyte in inverse relationship to the concentration of the first analyte in the fluid test sample or the analyte/labeled specific binding partner complex is bound to the immobilized specific binding partner in a direct relationship to the concentration of analyte in the fluid test sample; and the labeled specific binding partner which did not bind to the second region is carried by capillarity to the third region where it is captured by the capture means;

c) reading the second zone of the developed matrix on an instrument having a detector capable of measuring the signal from the detectable label to determine the concentration of the labeled binding partner in the second zone and reading the third zone of the developed strip in a similar manner to determine the signal from the labeled binding partner in the third zone of the matrix;

d) determining a final response signal by ratioing the signals from the labeled binding partner immobilized in the second region and the labeled binding partner captured in the third region;

e) determining the concentration of the first analyte in the fluid sample by comparing the final response signal determined in step (d) with final response signals determined in a similar manner for fluid samples containing known concentrations of the first analyte; and f) correcting the concentration of the first analyte determined in step (e) by determining the concentration of the second analyte in the fluid test sample by measuring the intensity of the signal in the fourth region of the matrix and converting this to a concentration value of the second analyte and then determining the ratio of the second analyte to the first analyte whose quantitative concentration is being sought.

DESCRIPTION OF THE INVENTION

Figure 1:
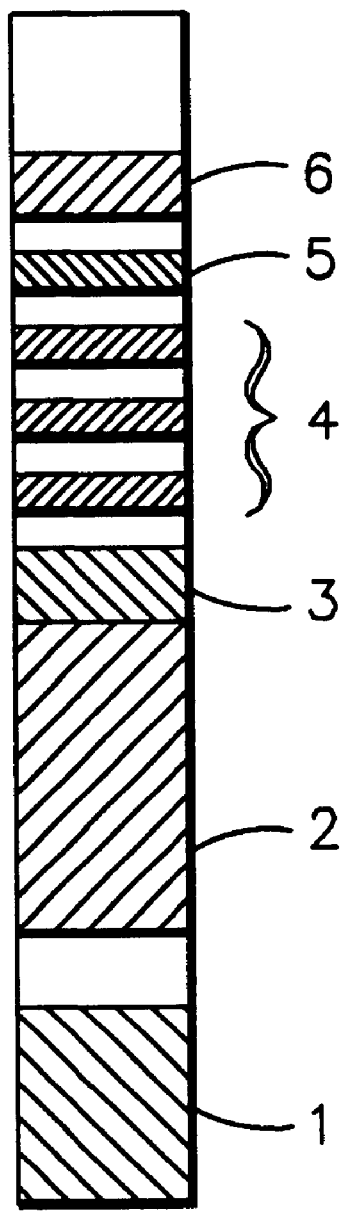
FIG. 1 is a representation of the type of immunochromatographic test strip upon which the method of the present invention can be carried out.

The present invention is practiced by first providing the test matrix through which the fluid test sample can flow by capillarity. Typically, the matrix will be in the form of a strip through which the test fluid flows horizontally. While the matrix could be assembled in a layered format through which the test fluid could flow vertically from top to bottom or vice-versa, the following discussion is focused on the preferred strip format.

The strip can be prepared from any matrix material through which the test fluid and an analyte contained therein can flow by capillarity and can be of a material which is capable of supporting non-bibulous lateral flow. This type of flow is described in U.S. Pat. No. 4,943,522 as liquid flow in which all of the dissolved or dispersed components of the liquid are carried through the matrix at substantially equal rates and with relatively unimpaired flow, as contrasted to preferential retention of one or more components as would be the case if the matrix material were capable of absorbing or imbibing one or more of the components. An example of such a matrix material is the high density or ultra high molecular weight polyethylene sheet material from Porex Technologies. Equally suitable for use as the matrix from which the chromatographic strips can be fabricated are bibulous materials such as paper, nitrocellulose and nylon.

Various immunochromatographic strip formats are suitable for use in conjunction with the present invention. A particularly suitable format is that which is disclosed in U.S. Pat. No. 4,446,232 in which there is described a device for the determination of the presence of antigens, which device comprises a strip of matrix material having a first zone in which there are provided immobilized analyte and enzyme linked antibodies specific to the analyte to be determined. The labeled antibodies can flow to a second zone when reacted with analyte introduced into the first zone via the test sample but will not so flow in the absence of analyte in the test fluid due to their being bound in the first region by interaction with the immobilized analyte. The analyte is typically antigen, although the format can be designed to detect the presence of antibodies as analyte. Modifications to this format are disclosed in U.S. Pat. No. 4,868,108. In another modification, the enzyme substrate is disposed in the region of a second, immobilized antibody to thereby capture the complex formed between the enzyme labeled binding partner and the analyte. This sort of format is particularly suitable for adaptation to the present invention, although any physically detectable signal generator may be used as the label since the present invention need not be limited to the interaction of an enzyme and its substrate to provide the detectable signal. Thus, by immobilizing the conjugate in a discrete detection zone located downstream on the strip from the zone in which the labeled binding partner for the analyte is captured, there are provided two regions from which the physically detectable property of the label can be measured to determine its concentration. By measuring the signal from the detectable label in the second region of the matrix (sometimes referred to as the capture zone) and the signal from the physically detectable property of the label in the third region (sometimes referred to as the detection zone), in which an immobilized antibody against the labeled binding partner (e.g. anti-mouse IgG when the labeled binding partner is an antibody) is the capture means, and determining the ratio of these signals, the accuracy of the test for analyte concentration can be increased. The accuracy is increased because this technique corrects for inaccuracies in labeled conjugate deposition and/or non-uniform flow through the matrix. More particularly, since the aforementioned inaccuracies of labeled conjugate deposition and non-uniform fluid flow are usually of small but significant magnitude, they do not substantially disturb the binding equilibrium. Therefore the ratio of the signals in the two binding regions is a more accurate measure of the analyte concentration than is the signal from either region by itself. This principle applies with equal force when the previously described sandwich format is used.

The second and third zones of the matrix used in the present invention may each be divided into two or more bands with the second region preferably containing 1 to 3 discrete bands and the third region having 1 to 2 bands. By dividing these regions into bands it is possible to increase the dynamic range and/or precision of the assay due to the non-linearity of reflectance to the number of detected labeled binding partners. Dividing the regions into discrete bands can be desirable because the measurement of small changes in detected labeled binding partner is more robust at higher values of reflectance than at low values. The number of capture and/or collection bands which are desirable will depend on the particular assay for which the strip is designed since dividing the capture and collection zones into 2 or more discrete bands will increase the dynamic range of certain assays but not of others. Dynamic range refers to the fact that the overall signal can be increased if one focuses on more than a single capture or detection band within a zone. Thus, when the detectable label is one which is detectable by a reflectance meter, there can be a large nonlinearity of reflectance and the error associated with the reflectance meter used. For example, the difference between 70% R and 75% R represents a fairly small amount of detected label whereas the difference between 30% R and 35% R represents a high percentage of detected label. With the use of certain reflectance meters, the error in reflectance reading stays constant or increases as the reflectance value decreases. Thus, it can be advantageous to use one or more additional capture or detection bands if this places the reflectance reading at a higher value where it is more sensitive to particle concentration. In those assays in which a wide dynamic range is not necessary, simply reading and ratioing a single capture and a single detection region can give good quantitative results. This is illustrated by the following Example 1 in which deoxypyridinoline (DPD) is the first analyte, the capture zone is divided into 3 bands ($P_1$, $P_2$ and $P_3$) while the detection zone is a single band ($P_4$) and the decode algorithm for the DPD assay is $T/P_n$ where T is the summation of the signal from all four bands. Algorithms using these reagent band reflectance values are constructed in such a way as to maximize the signal to noise ratio and thereby increase the quantitation of the assay by reducing coefficients of variation (CV). The particular algorithm chosen will depend upon the number of reagent bands on the particular test strip being used and the sensitivity and/or precision of the assay. Once the appropriate algorithm is chosen, the relationship between the algorithm value and the analyte concentration is determined and fitted to a non-linear regression function. The purpose of such fitting is to minimize the error relating the chosen algorithm value to that of the analyte concentration. The regression function is used in order to determine a calibration curve which is used to relate the determined algorithm value to that of the analyte concentration. Once this relationship has been established, the calibration curve, which can be stored as an equation in the reflectance instrument, is used to calculate the analyte concentration.

Since the capture and detection zones' reflectance changes opposite to one another, i.e. the greater the signal from the capture zone the less the signal from the detection zone, the use of multiple capture and/or detection bands is designed to alter this range of reflectance values. The mechanism by which analyte concentration changes the band's reflectance is a function of the chemistry of a particular assay. For sandwich assays, with increasing analyte concentration, the capture band reflectance increases and the detection band reflectance decreases. For competitive assays, the capture band reflectance decreases and detection band reflectance increases with increasing amounts of analyte in the fluid test sample.

The need for additional capture and/or detection bands depends on whether changes in an additional band are significantly larger in a given analyte region than in any of the other bands. Depending upon the label (i.e. gold sol) concentration, additional capture bands will also reduce the signal changes at the detection zone. In certain assays, a second capture band simply mirrors the first capture band but with reduced signal changes, and, in such cases, its need can be questioned. However, in those assays in which the detection zone is too dark due to low reflectance, the addition of capture bands can reduce the signal in this zone.

In general, the crux of the present invention involves choosing a particular algorithm and additional capture and/or detection bands so as to alter the signal in such a way that it can be read with greater precision by a reflectance meter.

There are two steps involved in developing an appropriate algorithm. The first is to increase the signal to noise ratio to as high a level as possible. The second is to define an algorithm which easily fits an equation so that accurate values for any analyte concentration may be obtained. This is demonstrated by the following study involving a strip containing three bands (2 capture bands and one detection band). The two capture bands had different capture reagent concentrations with the first capture band having a 10-fold lower capture reagent concentration than the second. This format demonstrates that different combinations and concentrations of capture and collection bands can be used depending upon the unique properties of each assay. Data were taken (representing N=18 for each analyte level) using 3 different CLINITEK® 50 reflectance meters over a period of 2 days. Table 1 shows the Figure of Merit (FOM) differences between DPD levels of the various band reflectance changes and the use of various algorithms. The FOM is calculated as (Avg1−Avg2)/(SD1+SD2) where Avg1 and Avg2 are the mean measured values for analyte level 1 and analyte level 2 and SD1 and SD2 are the standard deviations of the mean values for analyte level 1 and analyte level 2.

TABLE 1

| | % R change | | FOM | | | | |
|---|---|---|---|---|---|---|---|
| | Cap 1 | Col 1 | Capture 1 | Detection 1 | Cap 1/Det 1 | Algor 1 | Total/Cap 1 |
| 0 to 10 | 3.8 | 6.1 | 1 | 1.39 | 1.56 | 1.94 | 2.07 |
| 10 to 25 | 4.6 | 5.9 | 1.21 | 1.51 | 2.51 | 2.08 | 2.12 |
| 25 to 50 | 4.9 | 5 | 1.36 | 1.39 | 2.18 | 2.22 | 2.39 |
| 50 to 75 | 5.1 | 2 | 1.5 | 0.48 | 1.98 | 1.99 | 1.94 |
| 75 to 150 | 7.1 | 3.6 | 2.37 | 0.84 | 2.07 | 3.05 | 2.91 |
| 150 to 250 | 2.1 | 1.7 | 0.72 | 0.49 | 1.18 | 1.06 | 0.93 |

In Table 1, Capture 1 is the infracted (R)corrected reflectance data for the Capture 1 band, detection band 1 is the IR corrected reflectance data for detection band 2, Cap1/Det1 is the K/S transformed data of Capture 1 where $K/S=(1-R)^2/2R$ divided by Detection 1 and Algor 1 is:

$$C/\{\text{Capture Band 2}/\Sigma\text{Capture Bands})*ABS(2-C)\}$$

where $C=100*(1+\Sigma(\text{Detection Bands}/\Sigma)\text{Reagent Bands}))$ and Total/Cap1 as:

$$\Sigma(\text{All Bands})/\text{Capture 1}$$

where ABS represents the absolute value of the number. In this illustration, the detection band performance decreases as the DPD concentration increases, whereas larger signal changes are noted for the capture band. For any algorithm, the goal is to weight the reflectance values in such a way that the signal to noise ratio in the region most critical to the assay is maximized. This can be accomplished by use of FOM analysis and Algor 1 is designed to weight the differences of the two capture bands higher at low analyte concentrations where this difference is greatest with that weighting of the collection band over the total at higher analyte concentrations. The other goal of Algor 1 is to place this weighting in a way which allows fitting to a common four parameter fit used in many immunoassays.

The second step in algorithm development is to use an equation which can be easily fitted and give accurate analyte concentrations for in between values. While FOM is a good method for distinguishing between two discrete analyte levels, it gives no information about the shape of the curve.

The best approach is often one that uses an analysis which mimics the chemistry of the particular assay. For immunoassays this is often a four parameter fit equation. The test for any fitted equation and algorithm is the use of random samples with various analyte concentrations and the calculation of the error (% CV) and bias. The goal is to seek the lowest % CV with minimal bias throughout the expected range of the assay. A comparison of the DPD results 0–250 nM/mM in urine for two types of analyses is shown in Tables 2 and 3 for the three band immunostrips used in this illustration.

TABLE 2

Algor 1 Results

| Expected Value | DPD | SD | % CV | Bias | DPD/Cr | SD | % CV |
|---|---|---|---|---|---|---|---|
| 0 | 2.8 | 2.8 | | 2.8 | 0.64 | | |
| 10 | 13.2 | 2.4 | 18.2 | 3.2 | 2.82 | 0.61 | 21.6 |
| 25 | 28.1 | 5.0 | 17.8 | 3.1 | 4.06 | 1.06 | 26.1 |
| 50 | 49.2 | 4.8 | 9.8 | −0.8 | 5.69 | 0.5 | 8.8 |
| 75 | 75.5 | 9.25 | 12.3 | 0.5 | 6.11 | 0.7 | 11.5 |
| 150 | 164.2 | 25 | 15.2 | 14.2 | 9.77 | 1.36 | 13.9 |
| 250 | 227 | 23.6 | 10.4 | −23 | 8.41 | 0.89 | 10.6 |

TABLE 3

Total/P1 Results

| Expected Value | DPD | SD | % CV | Bias | DPD/Cr | SD | % CV |
|---|---|---|---|---|---|---|---|
| 0 | 0.7 | 2.47 | | 0.723 | 0.03 | | |
| 10 | 10.7 | 2.34 | 22.0 | 0.663 | 2.2 | 0.56 | 25.5 |
| 25 | 27.4 | 5.51 | 20.1 | 2.383 | 3.93 | 1.18 | 30.0 |
| 50 | 51.6 | 4.59 | 8.9 | 1.598 | 5.78 | 0.49 | 8.5 |
| 75 | 80.3 | 9.99 | 12.4 | 5.33 | 6.29 | .905 | 14.4 |
| 150 | 158.8 | 15.9 | 10 | 8.807 | 8.98 | 1.05 | 11.7 |
| 250 | 205.6 | 31.1 | 15.1 | −44 | 7.38 | 1.22 | 16.6 |

From the data of Tables 2 and 3, it can be determined that for this particular analysis, the first algorithm has less error, as measured by the % CV, at all DPD values. This example illustrates the somewhat empirical method for finding a correct algorithm. The chosen algorithm will be one which has the lowest error associated with it for a given strip formulation and format and a given clinical range for the analyte.

After the value for the target analyte has been obtained, the instrument uses the reflectance value at one or more wavelengths of the reagent pad for the second analyte to determine the concentration of this analyte in the fluid test sample. In the case in which DPD is the target analyte and creatinine is the second analyte, the precision (or the reduction of signal to noise) is critical to the assay for both analytes. Absent a high level of precision, the resulting error will produce a test which has little medical significance since as little as a two fold increase in the DPD/creatinine ratio occurs between the normal and osteoporosis states. The second analyte is selected from those materials in the body fluid which are clinically related to the first analyte. The most notable example of a second analyte is creatinine, the end metabolite when creatine becomes creatine phosphate which is used as an energy source for muscle contraction. The creatinine produced is filtered by the kidney glomeruli and then excreted into the urine without reabsorption. In order to increase the sensitivity of urinary assays and minimize the problem of high urine flow rates which result in urine dilution, analyte/creatinine ratios are used in urine protein assays to normalize the urine concentration. Common creatinine assays include the alkaline Jaffe and Benedict-Behre methods which are run at a high pH, typically in the range of from 11.5 to 12.5. More recently, there has been developed a creatinine assay in which the urine sample is contacted with cupric ions in the presence of citrate, a hydroperoxide and an oxidizable dye which provides a colored response in the presence of oxygen free radicals and a pseudoperoxide. This method is more fully described in U.S. Pat. No. 5,374,561. Creatinine quantitation may also be accomplished immunologically as described in WO- 96/34271. Those second analytes whose concentration in the body fluid sample is clinically related to the concentration of the target analyte are not limited to creatinine in urine nor is urine the only body fluid which can be assayed by the method of the present invention. Thus, for example, the body fluid tested can be whole blood, the first (target) analyte can be $HbA_{1c}$ and the second analyte can be total hemoglobin since the apparent concentration of $HbA_{1c}$ can be adjusted to the whole blood's total hemoglobin concentration to factor out bias in the $HbA_{1c}$ assay. Inulin, administered intravenously, is, like creatinine, an indicator of renal flow. In serology based assays the first analyte can be total prostate specific antigen and the second analyte free prostate specific antigen. Another pair of analytes whose concentrations are clinically related are alanine aminotransferase (ALT) and aspartate aminotransferase (AST) which are widely distributed in human tissues. Both AST and ALT are normally present in human plasma, bile and saliva. With viral hepatitis and other forms of liver disease, levels of AST and ALT are elevated even before clinical signs of disease, such as jaundice, appear. In toxic or viral hepatitis, ALT is characteristically as high or higher than the ALT and the ALT/AST ratio, which is normally <1, approaches or becomes greater than unity. Furthermore, AST concentrations increase after myocardial infarction thereby changing the ratio of these two enzymes and their activity. Thus, clinically significant results can be obtained by determining the ratio of these two analytes in serum.

Many clinically significant target analytes are present in urine and are determinable by means of the present invention. Among these analytes are deoxypyridinoline (DPD), human serum albumin, drugs of abuse such as amphetamines/barbiturates/cocaine, clinically important protein markers such as prostate specific antigen, kidney disease proteins such as lactate dehydrogenase, N-acetyl-B-D-glucosamindase, pregnancy or fertility associated hormones such as human chorionic gonadotropin, follicle-stimulating hormone and lutenizing hormone, markers of urinary tract infection such as Tamm-Horsfall protein or lipopolysaccharide, beta-2-microglobulin, amylase and chlamydial LPS. Determining the ratio of IgA/IgG to assess infection can be accomplished by means of the present invention. Correcting their absolute concentrations for variations in renal flow by ratioing these concentrations to observed creatinine concentrations increases the precision and accuracy of the measurements.

While the means for detecting the signal from the developed strip will depend on the detectable label attached to the labeled binding partner, the use of a reflectance meter is typical when the label's detectable physical property is the reflectance of light at a predetermined wavelength in the visible or infrared region of the spectrum. In a preferred embodiment, there is provided a reflectance meter with means for moving the strip or the meter's detector element relative to each other such as by use of a specimen table for the strip which can be moved laterally under the readhead of the detector. This technique will assist in providing accurate quantitation for regions of the strip which may not have been precisely located with respect to the detection means of the reflectance meter. More specifically, the location of the strip relative to the detector can be under microprocessor control, so that the reflectance from the second, third or fourth regions of the strip, and individual bands within these regions, can be individually determined.

The method of practicing the present invention is more fully illustrated by the following examples:

EXAMPLE 1

A test strip for the determination of creatinine and deoxypyridinoline (DPD) containing six distinct areas assembled together onto a polystyrene backing of 4 inches (101.6 mm) in length and 0.2 inch (5.0 mm) in width is illustrated by FIG. 1. Referring to FIG. 1, area 1 is the creatinine pad with a size of 0.2×0.2 inch. The creatinine pad was prepared as follows to render it suitable for the colorimetric determination of creatinine: Whatman 3 mm filter paper was first treated by dipping it to a depth of 0.2 inch into a solution containing 30 mM copper sulfate, 50 mM citrate, 750 mM glycerol-2-phosphate, 0.2% hexane sulfonic acid, 50 mM phytic acid and 0.2% sodium dodecyl sulfonate (SDS) at pH 6.94. After drying, the strip was dipped into a solution containing 33 mM 3,3',5,5'-tetramethylbenzidine, 73 mM diisopropylbenzene dihydroperoxide, 63 mM triisopropanolamine borate, 0.5% plasonde and 0.032% ethyl orange. The intensity of the colored response produced when the strip is contacted with an aqueous medium containing creatinine is proportionate to the concentration of creatinine. Area 2 is the buffer pad, prepared by impregnation of Whatman F075-07 glass fiber with 0.5 to 1 M glycine and 175 to 350 mM urea and having a size of 0.2×0.5 inch (12.7 mm). The buffer pad serves the purpose of buffering the pH of urine samples to the desired value. For example, the pH of urine can range from 4.5 to 8 and a buffer pad can be used to keep the samples at a pH >7 to favor the antigen/antibody bonding reaction. There is a 0.1 inch (2.5 mm) gap between creatinine pad 1 and buffer pad 2 for purposes of isolating the creatinine reagent from the buffer pad reagent. Area 3 is a gold sol-DPD antibody pad (first region containing a labeled binding partner specific for the analyte). Areas 4 and 5 are the immunochromatography development area where the capture and detection reagents are deposited onto one piece of nitrocellulose having a size of 0.2×1.25 inch (31.75 mm). Area 4 contains three capture bands (second region containing immobilized analyte) with DPD immobilized to carboxyl terminated polyethylene glycol with a band width of about 0.059 inch (1.5 mm) per band and a 0.2 inch space between the bands (from center to center). At 0.2 inch from the center of the third capture band is area 5 consisting of one anti-IgG collection band (third region for immobilizing unreacted labeled binding partner) with, a band width of about 0.059 inch (1.5 mm). At 0.2 inch above the collection band is the absorbant pad 6 which serves to absorb the liquid which migrates from the nitrocellulose area of the strip having a size of 0.2 inch×0.5 inch (12.7 mm).

To perform the assay, the strip was dipped into the test solution, i.e. a urine sample containing the DPD analyte to be determined, for 3 seconds to a depth such that only the creatinine zone and buffer pad were below the surface of the test solution which allowed the test solution to flow up the strip by capillarity through the capture bands of the capture region, the single band of the detection region and to the absorbant pad. At the end of the 3 second dip the strip was placed on the read table of a CLINITEK® 50 reflectance spectrometer and the device's start button pressed. The creatinine pad reflectance was recorded at 3 minutes and the reflectance of the immuno DPD strip (all 4 bands) was measured and recorded at 3 minutes. Reflectance signals for the DPD assay were measured with IR and green filters whereas reflectance for the creatinine assay was measured using red and green filters. The device gives a response in decode values which is derived by equations 1 to 5.

$$\text{Decode for Creatinine} = \frac{[R]\text{green}}{[R]\text{red}}$$

where $[R]_{green}$ is the reflectance measured with the green filter, $[R]_{red}$ is the reflectance measured with the red filter.

For the DPD assay, the band response signals were esignated as indicated in Table 4.

TABLE 4

Band Signals Designation for DPD Assay

| Band # | Type | Designation |
|---|---|---|
| 1 | Capture band 1 | P1 |
| 2 | Capture band 2 | P2 |
| 3 | Capture band 3 | P3 |
| 4 | Collection band 1 | P4 |

The reflectance with the green filter is ratioed to the reflectance with the IR filter to reduce the error from the variations between strips such as height and surface variations. The reflectance at the IR wavelength remains fairly constant regardless of the gold sol intensity of the band. The corrected reflectance, [Rn], is calculated according to Equation 2.

$$[Rn] = \frac{[Rn]_{green} \times 65}{[Rn]_{IR}}$$

where n is the band number 1, 2, 3 or 4, $[Rn]_{green}$ is the reflectance of band n with green filter, $[Rn]_{IR}$ is the reflectance of band n with IR filter. The number 65 is the assigned corrected reference value since the % reflectance with the IR filter is about 65%.

The IR corrected reflectance value, [Rn], is then converted to K/S according to Equation 3 to give the band response signal for each band:

$$\text{Band Signal} = Pn = \frac{(1 - [Rn])^2}{2 \times [Rn]}$$

where band signal, Pn, is the K/S transformation reflectance value, [Rn].

The response decode of each band is finally computed according to Equation 4.

$$\text{Decode for } DPD \text{ assay} = T/P_1 \quad \text{Equation 4}$$

where T is the summation of the band signal for all bands (Equation 5).

$$T = \Sigma Pn$$

$$n=1 \text{ to } N \quad \text{Equation 5}$$

where N is the total number of capture bands and collection bands which is 4 in the present example, Pn is the band signal n and n is 1, 2, 3 or 4.

Figure 2:
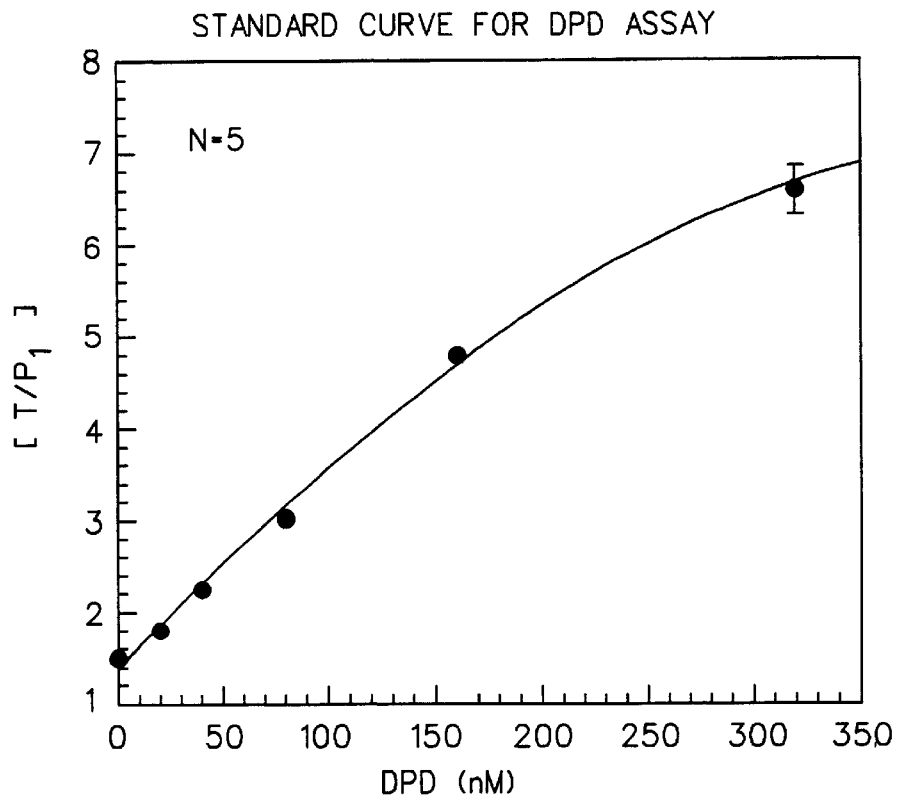
FIG. 2 is a standard curve for deoxypyridinium concentration as a function of the decode response from a CLINITEK® 50 instrument.
Figure 3:
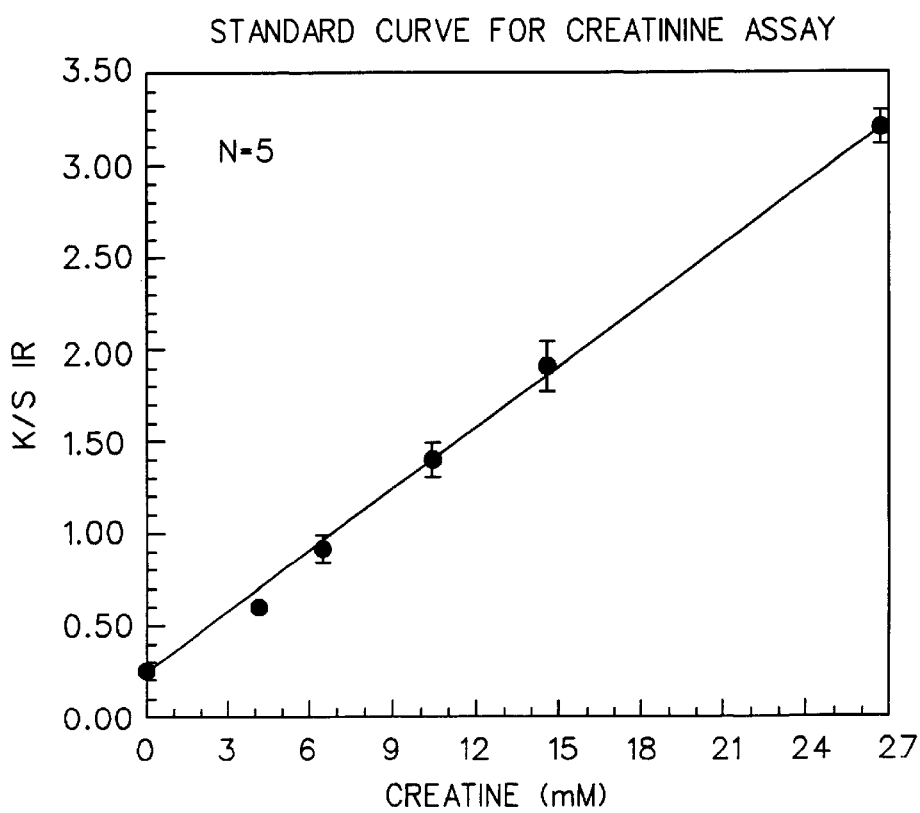
FIG. 3 is a standard curve for creatinine concentration as a function of the K/S value obtained using IR (infrared) radiation.

Standard curves for DPD and creatinine were generated using calibrators containing six levels of analyte concentrations. Examples of standard curves are shown in FIG. 2 for the DPD assay and FIG. 3 for the creatinine assay. The DPD and creatinine concentrations for the urine test sample were calculated from the DPD and creatinine standard curves respectively. The DPD/creatinine ratio in nM/mM was then calculated for urine sample A as per the following calculation:

DPD concentration calculated from the DPD standard curve=123 nM

Creatinine concentration calculated from the creatinine standard curve=10.2 mM

The DPD/creatinine ratio=123 nM/10.2 mM=12.1 nM/mm.

The cutoff for determination of a state of high bone resorption is a DPD/creatinine ratio is 7.4 nM/mM. Lower than 7.4 is normal and larger than 7.4 is at the state of high bone resorption. Therefore, in this example, the result indicates a state of high bone resorption. A second urine sample was analyzed in a similar manner and gave the following results:

DPD concentration=123 nM

Creatinine concentration=20.5 mM

DPD/Creatinine ratio=6.0 nM/mM.

Although the DPD concentration is the same, the ratio of DPD to creatinine indicates a state of low bone resorption.

Five runs were made using the above procedure with urine samples containing varying amounts of DPD and creatinine. The expected and observed ratios as well as standard deviations, % coefficient of variance and positive/negative biases are set out in Table 5. From Table 5 it can be determined that a precision of less than 12% CV was obtained at three levels, 4.52, 7.54 and 12.07 nM/mM of DPD to creatinine.

TABLE 5

DPD/Creatinine Assay Performance

| Expected | Recovered | | | |
|---|---|---|---|---|
| DPD/CR nM/mM | DPD/CR nM/mM | SD | % CV | Bias nM/mM |
| 4.52 | 4.29 | 0.50 | 11.6% | −0.23 |
| 7.54 | 7.59 | 0.89 | 11.7% | 0.05 |
| 12.07 | 12.04 | 1.38 | 11.5% | −0.03 |

Average % CV = 11.9%

While the gold sol labeled antibodies are visually observable in the capture and collection zones of the strip, clinically meaningful results are obtainable only through the use of a reflectance meter. This is the case because of the use of multiple bands across the entire length of the strip. In addition, the band signals require reflectance measurement at different wavelengths (IR, green and red) using an instrument with the capability to measure and record the reflectance at these wavelengths. The reflectance measurements are ratioed based on a predetermined algorithm using the instrument's software. Furthermore, the analyte concentrations are determined using standard curves stored in the instrument and the DPD/creatinine ratio is computed using the software set up in the instrument.

In the above example, the final response signal (decode) for the DPD assay was determined using the algorithm decode=[T/Pn] where T is the summation of the signal from all four bands and Pn is the band signal of band 1. The use of this algorithm enhances the, accuracy of the assay because ratioing the band signal minimizes the systematic error such as error introduced by instrument to instrument variation. Other algorithms may be used to determine the final response signal. The response signal in this example was determined as:

Response Signal=[T/Capture Band 1] or [T/$P_1$]

where all band signals are K/S transformation reflectance values and T is the summation of capture bands and detection bands.

The advantages of using band ratioing is demonstrated by the data of Tables 6 and 7 from which it can be determined that the precision with which the strip can determine the concentration of DPD is much greater than that which is obtainable when using only the signal from the capture zone.

TABLE 6

Response Signal = Band Ratioing Algorithm [T/P]

| Expected | Recovered | | |
|---|---|---|---|
| DPD/CR nM/mM | DPD/CR nM/mM | SD | % CV |
| 4.15 | 4.23 | 0.53 | 12.5 |
| 8.09 | 8.10 | 0.28 | 3.5 |
| 10.37 | 10.44 | 1.16 | 11.1 |

TABLE 7

Response Signal = Capture Zone [$P_1$] (no band ratioing)

| Expected | Recovered | | |
|---|---|---|---|
| DPD/CR nM/mM | DPD/CR nM/mM | SD | % CV |
| 4.15 | 2.84 | 4.1 | 144 |
| 8.09 | 7.74 | 0.46 | 6.0 |
| 10.37 | 10.99 | 2.0 | 18.5 |

Alternatively, the final response signal can be calculated as:

Response Signal=[Detection Band/Capture Band]

where all band signals are K/S transformation reflectance values. Alternatively, when the strip contains multiple capture bands and detection bands, the final response signal can be calculated as:

[Capture Band 1/Detection Band 1]

where all signals are K/S transformation reflectance values. Another method of calculating the response signal involves using the algorithm:

Response Signal=[$W_{cap}$* Capture Band 1/$W_{det}$* Detection Band]

where all band signals are reflectance values and the $W_{cap}$ and $W_{det}$ are weighting functions which weight the capture bands and detection bands differently. Thus, a large number of algorithms can be used to determine the final response signal.

The calculation of the response signal by ratioing the signals from the labeled binding partner immobilized in the second (capture) region of the strip and the labeled binding partner immobilized in the third (detection) region is critical to increasing the precision of the assay by reducing the signal to noise ratio. This enhanced precision is necessary for the test to have clinical significance since only a two-fold increase in the DPD/creatinine ratio occurs between the normal and disease indicating osteoporosis states.

Further evidence of the improvement in analytical results that can be achieved by the present invention is presented in Tables 8–10. These table were prepared using the same data set but 3 different algorithms ([T/$P_1$] with band ratioing, % reflectance of first capture band with no IR correction and no band ratioing and % reflectance of first capture band with no band ratioing but with IR correction) are compared.

TABLE 8

Performance Using [T/P₁] Band Ratioing Algorithm

| Expected DPD, nM | Recovered DPD, nM | | | | | Expected ratio | DPD/CR, nM/mM | | | | |
|---|---|---|---|---|---|---|---|---|---|---|---|
| | mean | sd | % CV | Bias | % Bias | | mean | sd | % CV | Bias | % Bias |
| 11 | 12.3 | 2.0 | 16.13 | 1.29 | | 4.1 | 4.2 | 0.7 | 16.71 | 0.08 | 1.97 |
| 33 | 29.6 | 2.8 | 9.44 | -3.35 | -10.16 | 1.7 | 1.4 | 0.2 | 13.36 | -0.21 | -12.71 |
| 72 | 70.8 | 4.3 | 6.11 | -0.66 | -0.93 | 8.1 | 8.1 | 0.2 | 2.68 | -0.01 | -0.17 |
| 110 | 116.8 | 2.0 | 1.74 | 6.85 | 6.22 | 20.7 | 23.1 | 0.6 | 2.77 | 2.34 | 11.28 |
| 165 | 159.9 | 9.3 | 5.80 | -5.14 | -3.12 | 12.4 | 12.4 | 0.9 | 6.87 | -0.05 | -0.37 |
| 275 | 275.8 | 12.7 | 4.61 | 0.78 | 0.28 | 10.4 | 10.6 | 1.2 | 10.94 | 0.22 | 2.08 |
| | | mean | 5.54 | | -1.54 | | | mean | 7.32 | | 0.35 | note:
the first level was excluded in the mean calculation

TABLE 9

Performance using % R of Capture Band 1
With No Band Ratioing and No IR Correction

| Expected DPD, nM | Recovered DPD, nM | | | | | Expected ratio | DPD/CR, nM/mM | | | | |
|---|---|---|---|---|---|---|---|---|---|---|---|
| | mean | sd | % CV | Bias | % Bias | | mean | sd | % CV | Bias | % Bias |
| 11 | 7.5 | 10.3 | 133.26 | -3.55 | | 4.1 | 2.9 | 4.1 | 143.86 | -1.30 | -31.29 |
| 33 | 38.3 | 14.9 | 38.90 | 5.30 | 16.06 | 1.7 | 1.9 | 0.8 | 42.11 | 0.24 | 14.52 |
| 72 | 69.7 | 4.6 | 6.60 | -1.80 | -2.52 | 8.1 | 7.9 | 0.5 | 6.33 | -0.19 | -2.33 |
| 110 | 114.9 | 10.9 | 9.49 | 4.90 | 4.45 | 20.7 | 21.7 | 2.0 | 9.22 | 0.96 | 4.64 |
| 165 | 159.1 | 20.1 | 12.63 | -5.90 | -3.58 | 12.4 | 12.0 | 1.3 | 10.83 | -0.44 | -3.56 |
| 275 | 264.3 | 27.7 | 10.48 | -10.70 | -3.89 | 10.4 | 10.0 | 1.6 | 16.00 | -0.37 | -3.56 |
| | | mean | 15.62 | | 2.11 | | | mean | 16.90 | | -3.60 | note:
the first level was excluded in the mean calculation

TABLE 10

Performance Using % R of Capture Band
With No Band Ratioing But With IR Correction

| Expected DPD, nM | Recovered DPD, nM | | | | | Expected ratio | DPD/CR, nM/mM | | | | |
|---|---|---|---|---|---|---|---|---|---|---|---|
| | mean | sd | % CV | Bias | % Bias | | mean | sd | % CV | Bias | % Bias |
| 11 | 7.4 | 10.1 | 136.49 | -3.60 | | 4.1 | 2.8 | 4.1 | 146.43 | -1.35 | -32.49 |
| 33 | 38.8 | 13.4 | 34.54 | 5.80 | 17.58 | 1.7 | 2.0 | 0.7 | 35.00 | 0.34 | 20.55 |
| 72 | 68.2 | 1.4 | 2.05 | -3.30 | -4.62 | 8.1 | 7.7 | 0.5 | 6.49 | -0.39 | -4.80 |
| 110 | 116.9 | 7.1 | 6.07 | 6.90 | 6.27 | 20.7 | 22.0 | 1.2 | 5.45 | 1.26 | 6.08 |
| 165 | 158.2 | 16.0 | 10.11 | -6.80 | -4.12 | 12.4 | 11.9 | 0.9 | 7.56 | -0.54 | -4.37 |
| 275 | 288.8 | 40.6 | 14.06 | 13.80 | 5.02 | 10.4 | 11.0 | 2.0 | 18.18 | 0.63 | 6.08 |
| | | mean | 13.37 | | 4.03 | | | mean | 14.54 | | -1.49 |

What is claimed is:

1. A method for determining the concentration of an analyte in a sample of body fluid which comprises the steps of:

a) providing a test matrix in the form of a strip through which the fluid sample can flow by capillarity, said strip having a first region which contains mobile specific binding partner for the analyte which binding partner bears a visually detectable label and can react with the analyte to form an analyte/labeled binding partner complex, at least one second region which contains immobilized analyte or an immobilized binding partner which is specific for an epitope of the analyte different than that to which the labeled binding partner is specific, at least one third region which contains means for capturing the analyte/labeled specific binding partner complex which is not bound in the second region and a fourth region which contains means for calorimetrically producing a visually detectable signal the intensity of which corresponds to the level of a second analyte in the sample of body fluid whose concentration is clinically related to that of the first analyte whose concentration is being determined;

b) developing the matrix by applying a sample of a body fluid suspected of containing the first and second analytes thereto thereby allowing it to contact the labeled specific binding partner so that analyte present in the fluid sample binds to the labeled specific binding partner to form a complex while leaving excess, unreacted labeled binding partner free to further react whereby the fluid sample carries the analyte/labeled binding partner complex and unreacted labeled binding partner along the matrix by capillarity to the second region containing the immobilized analyte in which region unreacted labeled binding partner is bound to the immobilized analyte in inverse relationship to the concentration of the first analyte in the fluid tests sample or the analyte/labeled specific binding partner complex is bound to the immobilized specific binding partner in a direct relationship to the concentration of first analyte in the fluid test sample; and the labeled specific binding partner which did not bind to the second region is carried by capillarity to the third region where it is immobilized by the immobilization means;

c) reading the second region of the developed matrix on a reflectance meter having a detector capable of measuring the visible signal from the visually detectable label to determine the concentration of the visually labeled binding partner in the second zone and reading the third zone of the developed strip in a similar manner to determine a signal from the labeled binding partner in the third zone of the matrix;

d) determining the final response signal by ratioing the signals from the labeled binding partner captured in the second region and the labeled binding partner immobilized in the third region;

e) determining the concentration of the first analyte in the fluid sample by comparing the final response signal determined in step d with final response signals determined in a similar manner for fluid samples containing known concentrations of the first analyte; and f) correcting the concentration of the first analyte as determined in step e by determining the concentration of the second analyte in the fluid test sample by measuring the intensity of the signal in the fourth region of the strip using a reflectance meter and then determining the ratio of the second analyte to the first analyte whose quantitative concentration is being sought.

2. The method of claim 1 wherein the body fluid is urine, whole blood, plasma, serum, sweat or saliva.

3. The method of claim 2 wherein the body fluid is whole blood, the first analyte is $HbA_{1c}$ and the second analyte is total hemoglobin.

4. The method of claim 2 wherein the body fluid is serum, the first analyte is transferrin and the second analyte is transferrin-iron binding capacity.

5. The method of claim 2 wherein the body fluid is urine, the first analyte is a urine born substance and the second analyte is a material whose concentration is a measure of renal clearance.

6. The method of claim 5 wherein the second analyte is creatinine or inulin.

7. The method of claim 6 wherein the first analyte is deoxypyridinoline, human serum albumin, amphetamines, barbituates, cocaine, prostate specific antigen, lactate dehydrogenase, N-acetyl-B-D-glucosamindase, human chorionic gonadotropin, follicle stimulating hormone, lutenizing hormone, Tamm-Horsfall protein, lipopolysaccharide, beta-2-microglobulin, amylase and chlamydial LPS.

8. The method of claim 2 wherein the body fluid is whole blood or serum, the first analyte is total prostate specific antigen and the second analyte is free prostate specific antigen.

9. The method of claim 1 wherein the first analyte is alanine aminotransferase and the second analyte is aspartate aminotransferase.

10. The method of claim 1 wherein the matrix is in the form of a strip through which the fluid sample flows horizontally.

11. The method of claim 1 wherein the second region of the test matrix is divided into 3 discrete bands, the third region is a single band and the final response signal is determined by solving the equation:

$$\text{Response Signal} = [T/P_1]$$

where T is the summation of the signal from all four bands and $P_1$ is the first band of the second region.

12. The method of claim 1 wherein the second and third regions of the test matrix are divided into multiple capture and detection bands respectively and the final response signal is determined by solving the equation:

$$\text{Response Signal} = \text{Capture Band 1/Detection Band 1}$$

where capture band 1 is the signal from the first band of the second region and detection band 1 is the signal from the first band of the third region.

13. The method of claim 1 wherein the strip is read by use of a reflectance meter which is equipped with software which is pre-programmed with the appropriate algorithm for the determination of the final response signal from reflectance signals received from the first and second regions and for the determination of the concentration of the second analyte from the reflectance signal received from the fourth region and for the determination of the ratio of the concentration of the second analyte in the sample of body fluid to the concentration of the first analyte to determine the corrected concentration of the first analyte.

\* \* \* \* \*

UNITED STATES PATENT AND TRADEMARK OFFICE
CERTIFICATE OF CORRECTION

PATENT NO. : 6,436,721 B1
DATED : August 20, 2002
INVENTOR(S) : Hai-Hang Kuo et al.

It is certified that error appears in the above-identified patent and that said Letters Patent is hereby corrected as shown below:

Column 2,
Line 2, "calorimetrically" should read -- colorimetrically --.

Column 6,
Line 37, "infracted (R)" should read -- infrared (IR) --.

Column 10,
Line 9, "esignated" should read -- designated --.

Column 12,
Table 6, line 7, "[T/P]" should read -- [T/$P_1$] --.

Column 13,
Table 9, column heading % CV under Recovered DPD, nM, the number "133.26" should read -- 138.26 --.

Column 14,
Lines 53-54, "calorimetrically" should read -- colorimetrically --.

Column 15,
Line 5, "tests" should read -- test --.

Signed and Sealed this

Tenth Day of June, 2003

JAMES E. ROGAN
*Director of the United States Patent and Trademark Office*